United States Patent
Shin et al.

(10) Patent No.: US 10,766,933 B2
(45) Date of Patent: Sep. 8, 2020

(54) MUTATED IMMUNOGLOBULIN-BINDING PROTEIN HAVING INCREASED ALKALINE TOLERANCE

(71) Applicant: Amicogen, Inc., Gyeongsangnam-do (KR)

(72) Inventors: Yong Chul Shin, Gyeongsangnam-do (KR); Zhe Piao, Gyeongsangnam-do (KR); Su-Lim Choi, Gyeongsangnam-do (KR); Yang Ho Jo, Gyeongsangnam-do (KR); So-Young Park, Gyeongsangnam-do (KR); Dae Beom Kwon, Gyeongsangnam-do (KR)

(73) Assignee: Amicogen, Inc., Gyeongsangnam-do (KR)

( * ) Notice: Subject to any disclaimer, the term of this patent is extended or adjusted under 35 U.S.C. 154(b) by 0 days.

(21) Appl. No.: 16/240,074

(22) Filed: Jan. 4, 2019

(65) Prior Publication Data

US 2019/0202871 A1    Jul. 4, 2019

Related U.S. Application Data

(63) Continuation of application No. PCT/KR2017/007248, filed on Jul. 6, 2017.

(30) Foreign Application Priority Data

Jul. 6, 2016    (KR) .................. 10-2016-0085721

(51) Int. Cl.
  *C07K 14/31*    (2006.01)
  *B01D 15/38*    (2006.01)
  *C07K 1/12*     (2006.01)

(52) U.S. Cl.
  CPC .............. *C07K 14/31* (2013.01); *B01D 15/38* (2013.01); *C07K 1/122* (2013.01)

(58) Field of Classification Search
  None
  See application file for complete search history.

(56) References Cited

U.S. PATENT DOCUMENTS

| | | | |
|---|---|---|---|
| 9,051,375 B2 | 6/2015 | Li et al. | |
| 2006/0194950 A1* | 8/2006 | Hober | B01D 15/3809 530/350 |
| 2013/0274451 A1 | 10/2013 | Bjorkman et al. | |

FOREIGN PATENT DOCUMENTS

| | | |
|---|---|---|
| EP | 1992692 A1 | 11/2008 |
| EP | 2202310 A2 | 6/2010 |
| EP | 2557157 A1 | 2/2013 |
| JP | 2005-538693 A | 12/2005 |
| KR | 10-2004-0099368 A | 11/2004 |
| WO | 2012165544 A1 | 12/2012 |
| WO | 2013109302 A2 | 7/2013 |
| WO | 2017009421 A1 | 1/2017 |

OTHER PUBLICATIONS

Greenspan et al. 1999 (Defining epitopes: Its not as easy as it seems; Nature Biotechnology, 17:936-937) (Year: 1999).*

Minakuchi et al. 2013 (Remarkable alkaline stability of an engineered protein A as immunoglobulin affinity ligand: C domain having only one amino acid substitution; Protein Science 22: 1230-1238) (Year: 2013).*

Linhult et al. 2004 (Improving the Tolerance of a Protein A Analogue to Repeated Alkaline Exposures Using a Bypass Mutagenesis Approach; Proteins: Structure, Function, and Bioinformatics 55:407-416). (Year: 2004).*

Linhult, Martin el al., "Improving the Tolerance of a Protein A Analogue to Repeated Alkaline Exposures Using a Bypass Mutagenesis Approach", Proteins: Structure, Function, and Bioinformatics. 2004, vol. 55, No. 2, pp. 407-416 See abstract pp. 409-410; table 1; and figures 1-2.

Minakuchi, Kazunobu et al., "Remarkable Alkaline Slability of an Engineered Protein A as limmmoglobuiin Affinity Ligand: C Domain Havmg Only One Amino Acid Substitution", Protein Society, 2013. vol. 22, No. 9. pp. 1230-1238 See abstract: and pp. 1230, 1236-1237.

Pabst et al. Engineering of novel Staphylococcal Protein A ligands to enable milder elution pH and high dynamic binding capacity. Journal of Chromatography A, 1362 (2014) 180-185.

\* cited by examiner

*Primary Examiner* — Mary Maille Lyons

(74) *Attorney, Agent, or Firm* — Banner & Witcoff, Ltd.

(57) ABSTRACT

The present invention relates to a mutated immunoglobulin-binding protein having increased alkaline tolerance and, more specifically, to an immunoglobulin-binding protein in which, with respect to the A-domain of Staphylococcal protein A, or a functional variant thereof, an amino acid at a specific site is mutated and thereby exhibits an increased chemical stability at an alkaline pH value in comparison to a parental molecule. The present invention can provide an antibody-purifying immunoglobulin-binding protein ligand and matrix which have enhanced alkaline tolerance and accordingly enhanced stability in multiple times of alkaline cleaning.

7 Claims, 4 Drawing Sheets

Specification includes a Sequence Listing.

SEQUENCE LISTING

<160> NUMBER OF SEQ ID NOS: 32

<210> SEQ ID NO 1
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide sequence of protein A domain A

<400> SEQUENCE: 1
catatggctg acaacaattt caacaaagaa caacaaaatg ctttctatga aatcttgaac      60
atgcctaact tgaacgaaga acaacgcaat ggtttcatcc aaagcttaaa ggatgaccca     120
agtcaaagtg ctaaccttt agcagaagct aaaaagttaa atgaatctca agcaccgaaa     180
catcaacatc agcaccaata agcggccgc                                      209

<210> SEQ ID NO 2
<211> LENGTH: 58
<212> TYPE: PRT
<213> ORGANISM: Artificial Sequence
<220> FEATURE:
<223> OTHER INFORMATION: Description of Artificial Sequence: Synthetic
      amino acid sequence of protein A domain A

<400> SEQUENCE: 2

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant of protein A domain A(AEP1, N18H)

<400> SEQUENCE: 3

Ala Asp Asn Asn Phe Asn Lys Glu Gln Gln Asn Ala Phe Tyr Glu Ile
1               5                   10                  15

Leu His Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant of protein A domain A(AEP4, D36V)

<400> SEQUENCE: 4

Ala Asp Asn Asn Phe Asn Lys Glu Gln Gln Asn Ala Phe Tyr Glu Ile

```
                1               5                   10                  15
Leu Asn Met Pro Asn Leu Asn Glu Glu Gln Arg Asn Gly Phe Ile Gln
                    20                  25                  30

Ser Leu Lys Val Asp Pro Ser Gln Ser Ala Asn Leu Leu Ala Glu Ala
            35                  40                  45

Lys Lys Leu Asn Glu Ser Gln Ala Pro Lys
        50                  55
```

<210> SEQ ID NO 5
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant of protein A domain A(AEP5, N43Y/L)

<400> SEQUENCE: 5

```
Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
                    20                  25                  30

Ser Leu Lys Asp Asp Pro Ser Gln Ser Ala Tyr Leu Leu Ala Glu Ala
            35                  40                  45

Lys Lys Leu Asn Glu Ser Gln Ala Pro Lys
        50                  55
```

<210> SEQ ID NO 6
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant of protein A domain A(AEP6, N53S)

<400> SEQUENCE: 6

```
Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
                    20                  25                  30

Ser Leu Lys Asp Asp Pro Ser Gln Ser Ala Asn Leu Leu Ala Glu Ala
            35                  40                  45

Lys Lys Leu Ser Glu Ser Gln Ala Pro Lys
        50                  55
```

<210> SEQ ID NO 7
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant of protein A domain A(AEP2, N23L)

<400> SEQUENCE: 7

```
Ala Asp Asn Asn Phe Asn Lys Glu Gln Gln Asn Ala Phe Tyr Glu Ile
1               5                   10                  15

Leu Asn Met Pro Asn Leu Thr Glu Glu Gln Arg Asn Gly Phe Ile Gln
                    20                  25                  30

Ser Leu Lys Asp Asp Pro Ser Gln Ser Ala Asn Leu Leu Ala Glu Ala
            35                  40                  45

Lys Lys Leu Asn Glu Ser Gln Ala Pro Lys
        50                  55
```

<210> SEQ ID NO 8
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant of protein A domain A(AES3, N28W)

<400> SEQUENCE: 8

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Trp Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant of protein A domain A(maF)

<400> SEQUENCE: 9

Ala Asp Asn Asn Phe Asn Lys Glu Gln Gln Asn Ala Phe Tyr Glu Ile
1               5                   10                  15

Leu His Met Pro Asn Leu Leu Glu Glu Gln Arg Trp Gly Phe Ile Gln
            20                  25                  30

Ser Leu Lys Val Asp Pro Ser Gln Ser Ala Tyr Leu Leu Ala Glu Ala
        35                  40                  45

Lys Lys Leu Ser Glu Ser Gln Ala Pro Lys
    50                  55

<210> SEQ ID NO 10
<211> LENGTH: 198
<212> TYPE: DNA
<213> ORGANISM: Artificial Sequence
<220> FEATURE:
<223> OTHER INFORMATION: Description of Artificial Sequence: Synthetic
      pBC-mAF plasmid

<400> SEQUENCE: 10
atggctgaca caatttcaa caaagaacaa caaaatgctt tctatgaaat cttgcacatg      60
cctaacttgc ttgaagaaca acgctggggt ttcatccaaa gcttaaaggt tgacccaagt    120
caaagtgctt acctttagc agaagctaaa aagttaagtg aatctcaagc accgaaacat    180
caacatcagc accaataa                                                  198

<210> SEQ ID NO 11
<211> LENGTH: 239
<212> TYPE: PRT
<213> ORGANISM: Artificial Sequence
<220> FEATURE:
<223> OTHER INFORMATION: Description of Artificial Sequence: Synthetic
      amino acid sequence of 4mAF

<400> SEQUENCE: 11

Met Ala Asp Asn Asn Phe Asn Lys Glu Gln Gln Asn Ala Phe Tyr Glu
1               5                   10                  15

```
Ile Leu His Met Pro Asn Leu Leu Glu Glu Gln Arg Trp Gly Phe Ile
         20                  25                  30

Gln Ser Leu Lys Val Asp Pro Ser Gln Ser Ala Tyr Leu Leu Ala Glu
         35                  40                  45

Ala Lys Lys Leu Ser Glu Ser Gln Ala Pro Lys Gly Thr Ala Asp Asn
 50                  55                  60

Asn Phe Asn Lys Glu Gln Gln Asn Ala Phe Tyr Glu Ile Leu His Met
 65                  70                  75                  80

Pro Asn Leu Leu Glu Glu Gln Arg Trp Gly Phe Ile Gln Ser Leu Lys
                 85                  90                  95

Val Asp Pro Ser Gln Ser Ala Tyr Leu Leu Ala Glu Ala Lys Lys Leu
             100                 105                 110

Ser Glu Ser Gln Ala Pro Lys Gly Thr Ala Asp Asn Asn Phe Asn Lys
             115                 120                 125

Glu Gln Gln Asn Ala Phe Tyr Glu Ile Leu His Met Pro Asn Leu Leu
        130                 135                 140

Glu Glu Gln Arg Trp Gly Phe Ile Gln Ser Leu Lys Val Asp Pro Ser
145                 150                 155                 160

Gln Ser Ala Tyr Leu Leu Ala Glu Ala Lys Lys Leu Ser Glu Ser Gln
                165                 170                 175

Ala Pro Lys Gly Thr Ala Asp Asn Asn Phe Asn Lys Glu Gln Gln Asn
            180                 185                 190

Ala Phe Tyr Glu Ile Leu His Met Pro Asn Leu Leu Glu Glu Gln Arg
            195                 200                 205

Trp Gly Phe Ile Gln Ser Leu Lys Val Asp Pro Ser Gln Ser Ala Tyr
        210                 215                 220

Leu Leu Ala Glu Ala Lys Lys Leu Ser Glu Ser Gln Ala Pro Lys
225                 230                 235
```

<210> SEQ ID NO 12
<211> LENGTH: 711
<212> TYPE: DNA
<213> ORGANISM: Artificial Sequence
<220> FEATURE:
<223> OTHER INFORMATION: Description of Artificial Sequence: Synthetic
    pET-Fc plasmid

<400> SEQUENCE: 12

```
atggacaaaa ctcacacatg cccaccgtgc ccagcacctg aactcctggg gggaccgtca      60
gtcttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca gcccccatcg agaaaaccat ctccaaagcc     360
aaagggcagc cccgagaacc acaggtgtac accctgcccc catcccggga ggagatgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcac gaggctctgc acaaccacta cacgcagaag     660
agcctctccc tgtctccggg taaactcgag caccaccacc accaccactg a             711
```

```
<210> SEQ ID NO 13
<211> LENGTH: 236
<212> TYPE: PRT
<213> ORGANISM: Artificial Sequence
<220> FEATURE:
<223> OTHER INFORMATION: Description of Artificial Sequence: Synthetic
      amino acid sequence of wild type Fc

<400> SEQUENCE: 13

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Leu Glu His His His His His
225                 230                 235

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      EP-F primer

<400> SEQUENCE: 14
gcttgatatc gaattcctgc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      T7 primer

<400> SEQUENCE: 15
```
taatacgact cactataggg                                                      20

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence: Synthetic
      18-F primer
<220> FEATURE:
<221> NAME/KEY: modified_base
<222> LOCATION: (25)..(26)
<223> OTHER INFORMATION: a, c, t, or g

<400> SEQUENCE: 16
caaaatgctt tctatgaaat cttgnnkatg cctaacttga acgaag            46

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      18-R primer
<220> FEATURE:
<221> NAME/KEY: modified_base
<222> LOCATION: (21)..(22)
<223> OTHER INFORMATION: a, c, t, or g

<400> SEQUENCE: 17
cttcgttcaa gttaggcatm nncaagattt catagaaagc attttg            46

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic
      23-F primer
<220> FEATURE:
<221> NAME/KEY: modified_base
<222> LOCATION: (20)..(21)
<223> OTHER INFORMATION: a, c, t, or g

<400> SEQUENCE: 18
cttgaacatg cctaacttgn nkgaagaaca acgcaatggt ttc               43

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      23-R primer
<220> FEATURE:
<221> NAME/KEY: modified_base
<222> LOCATION: (23)..(24)
<223> OTHER INFORMATION: a, c, t, or g

<400> SEQUENCE: 19
gaaaccattg cgttgttctt cmnncaagtt aggcatgttc aag               43

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      28-F primer
<220> FEATURE:

```
<221> NAME/KEY: modified_base
<222> LOCATION: (17)..(18)
<223> OTHER INFORMATION: a, c, t, or g

<400> SEQUENCE: 20
gaacgaagaa caacgcnnkg gtttcatcca aagcttaaag                           40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      28-R primer
<220> FEATURE:
<221> NAME/KEY: modified_base
<222> LOCATION: (23)..(24)
<223> OTHER INFORMATION: a, c, t, or g

<400> SEQUENCE: 21
ctttaagctt tggatgaaac cmnngcgttg ttcttcgttc                           40

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      36-F primer
<220> FEATURE:
<221> NAME/KEY: modified_base
<222> LOCATION: (22)..(23)
<223> OTHER INFORMATION: a, c, t, or g

<400> SEQUENCE: 22
ggtttcatcc aaagcttaaa gnnkgaccca agtcaaagtg ctaac                     45

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      36-R primer
<220> FEATURE:
<221> NAME/KEY: modified_base
<222> LOCATION: (23)..(24)
<223> OTHER INFORMATION: a, c, t, or g

<400> SEQUENCE: 23
gttagcactt tgacttgggt cmnnctttaa gctttggatg aaacc                     45

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence: Synthetic
      43-F primer
<220> FEATURE:
<221> NAME/KEY: modified_base
<222> LOCATION: (21)..(22)
<223> OTHER INFORMATION: a, c, t, or g

<400> SEQUENCE: 24
atgacccaag tcaaagtgct nnkcttttag cagaagctaa aaag                      44

<210> SEQ ID NO 25
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      43-R primer
<220> FEATURE:
<221> NAME/KEY: modified_base
<222> LOCATION: (23)..(24)
<223> OTHER INFORMATION: a, c, t, or g

<400> SEQUENCE: 25 cttttagct tctgctaaaa gmnnagcact ttgacttggg tcat                44

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      52-F primer
<220> FEATURE:
<221> NAME/KEY: modified_base
<222> LOCATION: (25)..(26)
<223> OTHER INFORMATION: a, c, t, or g

<400> SEQUENCE: 26
cttttagcag aagctaaaaa gttannkgaa tctcaagcac cgaaacat           48

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      52-R primer
<220> FEATURE:
<221> NAME/KEY: modified_base
<222> LOCATION: (23)..(24)
<223> OTHER INFORMATION: a, c, t, or g

<400> SEQUENCE: 27
atgtttcggt gcttgagatt cmnntaactt tttagcttct gctaaaag          48

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      mAF-F primer

<400> SEQUENCE: 28
cggggtaccg ctgacaacaa tttcaacaaa g                             31

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      mAF-R primer

<400> SEQUENCE: 29
cggggtacct ttcggtgctt gagattcatt taac                          34

<210> SEQ ID NO 30
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      4mAF-F primer

<400> SEQUENCE: 30
cgccatatgg ctgacaacaa tttcaacaaa g                                    31

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      4mAF-R primer

<400> SEQUENCE: 31
ccgctcgagt ttcggtgctt gagattcatt taac                                 34

<210> SEQ ID NO 32
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide sequence of 4mAF

<400> SEQUENCE: 32
atggctgaca acaatttcaa caaagaacaa caaaatgctt tctatgaaat cttgcacatg    60
cctaacttgc ttgaagaaca acgctggggt ttcatccaaa gcttaaaggt tgacccaagt   120
caaagtgctt acctttttagc agaagctaaa aagttaagtg aatctcaagc accgaaaggt   180
accgctgaca acaatttcaa caaagaacaa caaaatgctt tctatgaaat cttgcacatg   240
cctaacttgc ttgaagaaca acgctggggt ttcatccaaa gcttaaaggt tgacccaagt   300
caaagtgctt acctttttagc agaagctaaa aagttaagtg aatctcaagc accgaaaggt   360
accgctgaca acaatttcaa caaagaacaa caaaatgctt tctatgaaat cttgcacatg   420
cctaacttgc ttgaagaaca acgctggggt ttcatccaaa gcttaaaggt tgacccaagt   480
caaagtgctt acctttttagc agaagctaaa aagttaagtg aatctcaagc accgaaaggt   540
accgctgaca acaatttcaa caaagaacaa caaaatgctt tctatgaaat cttgcacatg   600
cctaacttgc ttgaagaaca acgctggggt ttcatccaaa gcttaaaggt tgacccaagt   660
caaagtgctt acctttttagc agaagctaaa aagttaagtg aatctcaagc accgaaa     717
```

MUTATED IMMUNOGLOBULIN-BINDING PROTEIN HAVING INCREASED ALKALINE TOLERANCE

RELATED APPLICATION DATA

The present application is a continuation application, which claims priority to PCT application PCT/KR2017/007248 designating the Republic of Korea and filed on Jul. 6, 2017; which claims the benefit of Korean Patent Application No. 10-2016-0085721, filed on Jul. 6, 2016, the entire contents of which are hereby incorporated herein by reference in their entireties.

SEQUENCE LISTING

The instant application contains a Sequence Listing which has been filed electronically in ASCII format and is hereby incorporated by reference in its entirety. Said ASCII copy, created on May 18, 2020, is named 009041_00001_US_SL.txt and is 18,325 bytes in size.

TECHNICAL FIELD

The present invention relates to a mutated immunoglobulin-binding protein having increased alkaline tolerance. More specifically, the present invention relates to an immunoglobulin-binding protein exhibiting an increased chemical stability at alkaline pH values relative to a parent molecule which is domain A of *Staphylococcus* Protein A or a functional variant thereof wherein an amino acid at a specific position is mutated.

BACKGROUND OF THE INVENTION

When cultured in gene-manipulated animal cells, monoclonal antibodies are secreted into a medium and present in very low concentrations while being mixed with various proteins secreted from the cells and those proteins in the medium. Therefore, the removal of impurities other than the desired monoclonal antibodies is an important step in antibody production. Affinity chromatography using protein A, which is an antibody affinity ligand capable of selectively recovering monoclonal antibodies from a medium, is mainly used for the separation and purification of monoclonal antibodies.

After antibody purification, cleaning-in-place (CIP) is performed to remove various contaminants such as nucleic acids, lipids, proteins, and microorganisms remaining in the resin. In general, NaOH is the most widely used material among resin cleaners. However, since protein-based refining resins are vulnerable to the alkali, there is a limitation to use NaOH. Protein A is washed with NaOH because it is relatively stable even under alkaline conditions. However, in order to increase the cleaning efficiency more, protein improvement studies have been carried out to develop protein A that is stable even under alkaline conditions.

Protein A is the cell surface protein of *Staphylococcus aureus* and is composed of five highly homologous domains (E, D, A, B, and C domains) which have a structure consisting of three semi-parallel helices and two loops located between with about 58 amino acid residues. Based on the streptococcal strain-derived albumin-biding domain (streptococcal albumin-binding domain), Gulich replaced all Asn residues with other amino acids based on the fact that Asn residues were sensitive to the alkali, resulting in obtaining a protein having high thermal stability and stability against 0.5 N NaOH (Gulich et. al., J Biotechnol, 28(2), 169-178 (2000)). Linhult developed a type of Protein A which retains its structural stability toward repeated alkaline treatments using bypass mutagenesis approach. More specifically, F30 of the Z domain (G29A variant of the B domain) exists at the third helix position and thus does not interfere with antibody binding, while being a residue that affects the structural stability. In fact, when F30 was replaced with Ala, its affinity to IgG was similar to wild type, but its structural stability was reduced, resulting in weakening its to resistance to the alkali its. When Z (F30A) was used as a template and Asn residues were replaced with residues other than Asn existing at the same position in other domains (E, D, A, and C domains), that is, when it was changed to N23T, N28A, N6A and N11S, it was confirmed that its stability increased under the alkaline condition. However, considering that their alkali tolerance is lower than that of the wild type, in the case of N21A, N43E and N52A, in addition to simply replacing of Asn with other residues, it is also important to know what type of residues have been replaced (Linhult et. al., Proteins, 55(2), 407-416 (2004)).

Korean Patent No. 10-1307651 discloses a mutant immunoglobulin-binding protein in which N3A/N23T or N3A/N6DN23T in the B domain or Z domain has occurred, which has an increased chemical stability at alkaline pHs compared to its parent molecule. U.S. Pat. No. 9,051,375 describes mutant sequences with an increased resistance to the alkali by substituting with histidine, serine, aspartic acid or threonine at three positions of N3, N6 and N23 in the Z domain, respectively.

Further, U.S. Patent Application Publication No. US20100048876 describes a chromatographic matrix comprising a C domain with the 3rd to 6th residues from the N terminus removed and a wild-type C domain, which has an increased stability forward the alkali. Korean Patent No. 10-1464040 discloses affinity chromatography ligands and matrices comprising two to five C, B or Z domains with three or four consecutive amino acid deletions from the first amino acid of the N-terminus, and this matrix is characterized by low ligand degradation under alkaline conditions compared to wild type ligands.

As described above, as individual Protein A ligands, the increase in the alkali tolerance was confirmed by substituting several specific amino acids for asparagine residue or eliminating the N terminal residues. However, such an effect is limited, considering that substitution residues affect alkali tolerance.

DETAILED DESCRIPTION OF THE INVENTION

Technical Problem

Accordingly, the inventors of the present invention have made an effort to invent a Protein A ligand having an increased alkali tolerance by randomly substituting various amino acids for other residues besides asparagine using a random mutation method. As a result, the inventors have found that when amino acid residues at one or more position selected from the 18th, 36th, 43rd and 52nd positions are mutated in the domain A of Protein A or a functional variant thereof, an immunoglobulin-binding protein with increased alkali tolerance can be obtained, completing the present invention has been completed.

An aspect of the present invention is to provide an immunoglobulin-binding protein defined by SEQ ID NO: 2 or a functional variant thereof of which an amino acid residue at one or more positions selected from the group consisting of 18th, 36th, 43th and 52nd positions is mutated.

Another aspect of the present invention is to provide a polymer comprising the mutated protein as a protein unit which comprises two or more repeat units.

Another aspect of the present invention is to provide a polynucleotide comprising a nucleotide sequence encoding the immunoglobulin-binding protein or the polymer.

Another aspect of the present invention is to provide a vector comprising the polynucleotide.

Another aspect of the present invention is to provide a transformant transformed with the vector.

Another aspect of the present invention is to provide a matrix for chromatography wherein a plurality of ligands comprising the immunoglobulin-binding protein are coupled to a solid support.

Another aspect of the present invention is to provide a method for isolating an immunoglobulin, the method comprising using the mutated protein, or the polymer or the matrix according to the present invention.

Another aspect of the present invention is to provide a chromatographic method, the method comprising separating at one or more target compound from a liquid by adsorbing the mutated protein, the polymer, or the matrix according to the present invention.

Another aspect of the present invention is to provide an immunoglobulin protein isolated by the above described method.

Another aspect of the present invention is to provide a target compound separated by the above described method.

Technical Solution

An embodiment according to an aspect of the present invention provides an immunoglobulin-binding protein defined by SEQ ID NO: 2 or a functional variant thereof of which an amino acid residue at one or more positions selected from the group consisting of 18th, 36th, 43th and 52nd positions is mutated.

An embodiment according to another aspect of the present invention provides a polymer comprising the mutated protein as a protein unit which comprises two or more repeat units.

An embodiment according to another aspect of the present invention provides a polynucleotide comprising a nucleotide sequence encoding the immunoglobulin-binding protein or the polymer.

An embodiment according to another aspect of the present invention provides a vector comprising the polynucleotide.

An embodiment according to another aspect of the present invention provides a transformant transformed with the vector.

An embodiment according to another aspect of the present invention provides a matrix for chromatography wherein a plurality of ligands comprising the immunoglobulin-binding protein are coupled to a solid support.

An embodiment according to another aspect of the present invention provides a method for isolating an immunoglobulin, the method comprising using the mutated protein, the polymer, or the matrix according to the present invention.

An embodiment according to another aspect of the present invention provides a chromatographic method, the method comprising separating at one or more target compound from a liquid by adsorbing the mutated protein, the polymer, or the matrix according to the present invention.

An embodiment according to another aspect of the present invention provides an immunoglobulin protein isolated by the above described method.

An embodiment according to another aspect of the present invention provides a target compound separated by the above described method.

Hereinafter, the present invention will be described in detail.

The present invention provides an immunoglobulin-binding protein defined by SEQ ID NO: 2 or a functional variant thereof of which an amino acid residue at least one positions selected from the group consisting of 18th, 36th, 43th and 52nd positions is mutated.

The present inventors have completed the present invention by molecular designing a recombinant protein mutant in which the amino acid of A domain of Protein A was substituted with another amino acid, obtaining the mutant from the transformed cell using protein engineering and genetic engineering methods, and comparing the antibody-binding activity of the mutant under an alkaline condition, As used herein, the term 'protein' is used interchangeably with "polypeptide" or "peptide" and refers to a polymer of amino acid residues as commonly found in the native state of a protein.

As used herein, the term 'nucleic acid' or 'polynucleotide' refers to deoxyribonucleotides or ribonucleotides in the single- or double-stranded form. Unless otherwise limited, it also includes known analogs of natural nucleotides that hybridize to nucleic acids in a manner similar to naturally occurring nucleotides.

As used herein, the term 'expression' refers to the production of a protein or nucleic acid in a cell.

One letter code (three letter code) of amino acids used herein means the following amino acids according to standard abbreviations in the biochemistry:

A (Ala): Alanine; C (Cys): Cysteine; D (Asp): Aspartate; E (Glu): Glutamate; F (Phe): Phenylalanine; G (Gly): Glycine; H (His): Histidine; I (Ile): Isoleucine; K (Lys): Lysine; L (Leu): Leucine; M (Met): Methionine; N (Asn): Asparagine; O (Ply): Pyrrolysine; P (Pro): Proline; Q (Gln): Glutamine; R (Arg): Arginine; S (Ser): Serine; T (Thr): Threonine; U (Sec): Selenocysteine; V (Val): Valine; W (Trp): Tryptophan; Y (Tyr): Tyrosine.

As used herein, '(amino acid one letter code) (amino acid position)(amino acid one letter code)' means that the former amino acid is replaced with the latter amino acid at the corresponding amino acid position of the naturally occurring polypeptide. For example, N23R means that asparagine corresponding to the 23rd residue of the naturally occurring polypeptide is replaced with arginine. Further, 'slash (/)' in the latter amino acid means 'or'.

The present invention is a mutant protein in which an amino acid residue at any one or more positions selected from the group consisting of 18th, 36th, 43rd and 52nd positions is substituted in an amino acid sequence derived from at least one domain selected from the A, B, C or Z domain of Protein A, with an immunoglobulin affinity, wherein its chemical stability is improved in an alkaline condition in comparison with a pre-mutation protein.

The amino acid sequence derived from the pre-mutation domain is preferably a sequence of the A domain of the Protein A described in SEQ ID NO: 1 or an amino acid sequence derived from the A domain of Protein A described in SEQ ID NO: 2

In the present invention, the mutant protein comprises the amino acid sequence defined in SEQ ID NO: 2 or a functional variant thereof. The term 'functional variants' includes all analogous sequences comprising one or more additional mutations at an amino acid position that does not affect the affinity of the mutant protein for immunoglobulins or its improved chemical stability in environments with increased pH values.

In the amino acid residue before the mutagenesis, it is preferable that the amino acid residue corresponding to the 18th-position of the A domain in each domain is Asn, the amino acid residue corresponding to the 23rd-position of the A domain in each domain is Asn, the amino acid residue corresponding to the 28th-position of the A domain in each domain is Asn, the amino acid residue corresponding to the 36th-position of the A domain in each domain is Asp, the amino acid residue corresponding to the 43rd-position of the A domain in each domain is Asn, or the amino acid residue corresponding to the 52nd-position of the A domain in each domain is Asn In the present invention, it is preferable that the amino acid substitution mutation introduced into each domain of *Staphylococcus* Protein A is at least one selected from the group consisting of a mutation that substitutes His for Asn corresponding to the 18th-position in the A domain (N18H), a mutation that substitutes Val for Asp corresponding to the 36th-position in the A domain (D6V), a mutation that substitutes Tyr or Leu for Asn corresponding to the 43rd-position in the A domain (N43Y/L) and a mutation that substitutes Ser for Asn corresponding to the 52nd-position in the A domain (N52S).

Most preferably, the mutant A domain of the present invention is preferably a polypeptide in which the 18th asparagine is replaced with histidine (herein after referred to as “AEP1”, SEQ ID NO: 3, N18H), a polypeptide in which the 36th aspartate is replaced with valine (herein after referred to as “AEP4”, SEQ ID NO: 4, D36V), a polypeptide in which the 43th asparagine is replaced tyrosine (herein after referred to as “AEP5”, SEQ ID NO: 5, N3Y/L), or a polypeptide in which the 52nd asparagine is replaced with serine (herein after referred to as “AEP6”, SEQ ID NO: 6, N53S), in the polypeptide defined by SEQ ID NO: 2.

The present invention also provides an immunoglobulin-binding protein characterized by further comprising an amino acid residue mutation at the 23rd and/or 28th position, in addition to the amino acid mutation at least one position selected from the group consisting of the 18th, 36th, 43rd and 52nd positions.

Preferably, the mutation at the 23rd position is selected from the group consisting of N23T, N23A, N23E, N23H, N23K, N23L, N23P, N23S and N23Y, while the mutation at 28th position is selected from the group consisting of N28W, N28G, N28R, N28F, and N28I. More preferably, the 23rd asparagine is replaced with leucine (herein after referred to as “AEP2”, SEQ ID NO: 7, N23L) in the mutation at the 23rd position of the polypeptide, while the 28th asparagine is replaced with tryptophan (herein after referred to herein as “AES3”, SEQ ID NO: 8, N28W) in the mutation at 28th position of the polypeptide.

The present invention also provides a mutant protein wherein all of the amino acids at the 18th, 23rd, 28th, 36th, 43rd and 52nd positions are all substituted in the protein defined by SEQ ID NO: 2 or a functional variant thereof.

The mutant protein may preferably be a protein defined by SEQ ID NO: 9, comprising N18H, N23L, N28W, D36V, N43Y and N52S mutations in the protein defined by SEQ ID NO: 2 or a functional variant thereof.

The mutant proteins of the present invention are protein ligands that specifically bind to the Fc fragment of immunoglobulins such as IgG, IgA, IgD, IgE and IgM, and maintain their affinity for a longer period than their parent molecules in alkaline conditions.

The increased alkali tolerance of the mutant proteins according to the present invention is well illustrated in the Examples of the specification.

In an embodiment of the present invention, mutants having increased alkali tolerance by the primary and secondary modifications of the wild type A domain were invented, finally leading to a mutant that has significantly increased alkali tolerance compared to the wild type A domain by collecting the most alkaline resistant residues in each residue, Specifically, in the primary modification, a mutant library were prepared by using an error prone PCR method for a wild type A domain base (SEQ NO ID: 1), and searching for mutants with increased alkaline tolerance compared to the wild type, followed by selecting mutants in which there was a replacement with different amino acids at the N18, N23, N28, D36, N43 and N52 positions of the wild type A domain polypeptide (SEQ NO ID: 2), respectively. Specifically, mutants were selected in which N18 was replaced with histidine, N23 with leucine, N28 with tryptophan, D36 with valine, N43 with tyrosine, and N52 with serine, respectively.

In the secondary modification, a site-saturated mutant library was prepared for further improvement of the six amino acid residues (N18H, N23L N28W, D36V, N43Y, N52S) selected by the primary modification, followed by searching for mutants having increased resistance to alkali. As a result, there were selected mutants in which there was further replacement with different amino acids at the N23, N28, and N43 positions of the wild-type A domain polypeptide (SEQ NO ID: 2), respectively. Specifically, mutants were selected in which N23 was substituted with alanine, glutamic acid, histidine, lysine, leucine, proline, serine, or tyrosine. N28 was substituted with glycine, arginine, phenylalanine, or isoleucine; and N43 was replaced with leucine.

In an embodiment of the present invention, following the analysis of the alkali tolerance of the produced mutants, mAF (SEQ NO ID: 9) was invented in which all substitution residues inducing the greatest resistance at each position was introduced. It was confirmed that the alkali tolerance of the mutant was significantly increased as compared with its wild type.

The present invention also provides a polymer comprising the mutated protein described above as a protein unit wherein the polymer comprises two or more repeat units. That is, it provides a polymer protein such as a dimer, a trimer, a tetramer, and a pentamer of the above-mentioned protein monomer.

The polymer of the present invention also comprises at least one of the E, D, A, B, and C domains of *Staphylococcus Protein A.*

According to one embodiment of the present invention, when a tetramer of the protein of SEQ ID NO: 9 (herein after referred to as 4mAF, SEQ ID NO: 11) was prepared and immobilized on a resin, it was confirmed that the alkali tolerance was superior to that of the commercialized resin (Mabselect Sure, GE Healthcare).

On the other hand, the present invention provides a polynucleotide comprising a base sequence encoding the immunoglobulin-binding protein or the polymer, and a recombinant expression vector comprising the polynucleotide.

As used herein, the term ‘recombinant expression vector’ refers to a vector capable of expressing a target protein or a target nucleic acid (RNA) in a suitable host cells, and indicates a gene construct containing an essential regulatory element operatively linked so as to express a polynucleotide (gene) insert.

As used herein, the term 'operatively linked' refers to the functional linkage of a nucleic acid expression control sequence and a nucleic acid sequence encoding a target protein or RNA so as to perform its general functions. That is, a nucleic acid sequence (e.g., a polynucleotide sequence encoding the mutated A domain according to the present invention) encoding a protein or RNA is linked in such a manner that gene expression is possible by an expression control sequence. For example, a promoter and a nucleic acid sequence encoding a protein or RNA must be operably linked to affect the expression of the nucleic acid sequence. Operational linkage in recombinant vectors can be prepared using gene recombinant techniques well known in the art, while site-specific DNA cleavage and linkage are carried out using enzymes generally known in the art.

The recombinant expression vector of the present invention is characterized by comprising a polynucleotide encoding the mutated A domain. The polynucleotide sequences cloned into the vector according to the present invention may be operably linked to an appropriate expression control sequence, while the operably linked gene sequence and expression control sequence may be contained within an expression vector which further comprises a selection marker for selecting a host cell comprising the vector and/or a replication origin. In addition, the expression vector may contain an expression control sequence, and optionally a signal sequence for membrane targeting or secretion or a leader sequence as required, while the expression vector may be prepared in various manners according to its purposes. The term "expression control sequence" refers to a DNA sequence that controls the expression of an operatively linked polynucleotide sequence in particular host cells. Such an expression control sequence includes a promoter for driving transcription, any operator sequence for controlling transcription, a sequence encoding a proper mRNA ribosomal binding site, a sequence for controlling the termination of transcription and translation, an initiation codon, a termination codon, a polyadenylation A signal, an enhancer and the like. The promoter of the vector may be constitutive or inducible.

PhoA signal sequence, OmpA signal sequence, and the like may be used as signal sequence when the host is *Escherichia* species; α-amylase signal sequence, subtilisin signal sequence and the like when the host is *Bacillus subtilis*; MFα signal sequence, SUC2 signal sequence and the like when the host is yeast; insulin signal sequence, α-interferon signal sequence, antibody molecule signal sequence, and the like when the host is an animal cell, without being not limited thereto.

The expression vector of the present invention is not particularly limited as long as it is a vector conventionally used in the field of cloning, and includes, for example, a plasmid vector, a cosmid vector, a bacteriophage vector, and a viral vector, but is not limited thereto. Specifically, the plasmid includes a plasmid derived from *Escherichia coli* (pBR322, pBR325, pUC118 and pUC119, pET-22b (+)), a plasmid derived from *Bacillus subtilis* (pUB110 and pTP5), and a plasmid derived from yeast (YEp13, YEp24 and YCp50), and the like, while the virus may be an animal virus such as retrovirus, adenovirus or vaccinia virus, an insect virus such as baculovirus, but is not limited thereto.

The present invention provides a transformant transformed with said expression vector.

The transformation includes any method of introducing the nucleic acid (A polynucleotide encoding the mutated A domain of the present invention) into an organism, cell, tissue or organ, and can be carried out by selecting a suitable standard technique depending on the type of host cell as known in the art. Such methods include electroporation, protoplast fusion, calcium phosphate ($CaPO_4$) precipitation, calcium chloride ($CaCl_2$) precipitation, silicon carbide whiskers, sonication, *Agrobacterium*-mediated transformation, polyethylenglycol (PEG) precipitation, dextran sulfate, lipofectamine, heat shock, particle gun bombardment, and the like, but is not limited thereto, The host cell refers to a prokaryotic or eukaryotic cell comprising heterologous DNA introduced there into by any means (for example, electric shock method, calcium phosphatase precipitation method, microinjection method, transformation method, viral infection, etc.).

In the present invention, the host cell may be any kind of single cell organisms commonly used in the field of cloning, for example, prokaryotic microbes such as various bacteria (Such as Clostridia genus, *E. coli*, etc.), lower eukaryotic microbes such as yeast, and cells derived from higher eukaryotes, including insect cells, plant cells, mammals and the like, but is not limited thereto. Since the expression level of the protein and the like vary depending on the type of the host cell, a host cell most suitable for a desired purpose can be selected and used by a person skilled in the art.

In the present invention, the host cell may be any genus microorganism selected from the group consisting of Clostridia spp. (such as *Clostridium acetobutylicum, Clostridium beijerinckii Clostridium saccharoperbutylacetonicum*, or *Clostridium saccharobutylicum* etc.), *Escherichia* spp., *Acetobacter* spp. (such as *Acetobacter turbidans, Acetobacter pasteurianus* etc), *Aeromonas* spp., *Alcaligenes* spp., *Aphanocladium* spp., *Bacillus* spp., *Cephalosporium* spp., *Flavobacterium* spp., *Kluyvera* spp., *Mycoplana* spp., *Protaminobacter* spp., *Pseudomonas* spp. and *Xanthomonas* spp. (such as *Xanthomonas citri* etc.), but is not limited thereto The mutated A domain polypeptide (protein) of the present invention may be naturally derived or constructed by a genetic engineering method. For example, a nucleic acid encoding the mutated A domain polypeptide is constructed by a conventional method. The nucleic acid can be constructed by PCR amplification using appropriate primers. Alternatively, DNA sequences may be synthesized by standard methods known in the art, for example, using an automated DNA synthesizer (Biosearch or Applied Biosystems). The constructed nucleic acid is inserted into a vector, which contains one or more expression control sequences (e.g., promoters, enhancers, etc.) that are operatively linked to the nucleic acid and control the expression of the nucleic acid, and the recombinant expression vector constructed therefrom is used to transform host cells. The prepared transformant is cultured and the mutated protein of the present invention is recovered from a culture product. The culture product may mean a culture supernatant, a cultured cell or microbial cell, or the debris of a cell or microbial cell. After the culture, when the modified protein of the present invention is produced in a microbial cell or cell, the microbial cell or cell is disrupted by using an ultrasonic treatment, a repeated freeze-thawing, or the like to collect the protein. In addition, when the protein is produced extracellularly, a culture solution is used as it is, or the microbial cells or cells are removed by centrifugation or the like. Thereafter, the separation and purification of the mutated A domain protein can be carried out by using the method of separating the protein with various chromatographic methods or slightly modified methods according to the purpose of the experiment, using the known properties of the A domain. It is also possible to purify the mutated A domain by an affinity chromatography method using specific binding affinity properties such as the binding affinity of the histidine peptide and the nickel column component, cellulose binding domain (CBD) and cellulose, and the like.

To confirm whether the modified and purified protein of the present invention is a protein of the desired amino acid sequence, a sample containing the protein is analyzed. As an analysis method, SDS-PAGE, Western blotting, mass spectrometry, amino acid analysis, amino acid sequencer, etc. can be used.

Herein, the term "substantially pure polypeptide" means that the polypeptide according to the present invention does not substantially contain any other protein derived from the host cells. For genetic engineering methods for the polypeptide synthesis of the present invention can be referenced in the following references can be referred to: Maniatis et al., Molecular Cloning; A laboratory Manual, Cold Spring Harbor laboratory, 1982; Sambrook et al., supra; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

The mutated A domain of the present invention can be used in a free state as well as in a immobilized state. The immobilization of the mutated A domain can be carried out by a conventional method known in the art, as a carrier including natural polymers such as cellulose, starch, dextran and agarose; synthetic polymers such as polyacrylamide, polyacrylate, polymethacylate, and Eupergit C; or minerals such as silica, bentonite and metal can be used. The mutated A domain may be conjugated to the carriers by covalent bond, ionic bond, hydrophobic bond, physical adsorption, microencapsulation, and the like. It is also possible that these carrier-enzyme conjugates form a covalent bond by the action of glutaraldehyde, cyanogen bromide or the like, thereby immobilizing the mutated A domain. In addition, without purifying the mutated A domain separately, but it is also possible to fix the microorganism cell containing the mutated A domain as it is. In such a case of whole cell immobilization such techniques as puncturing cells or surface expression may be applied to increase the reactivity of the mutated A domain contained in the microorganism.

The present invention also provides a matrix for chromatography wherein a plurality of ligands comprising the immunoglobulin-binding protein are coupled to a solid support.

The matrix according to the present invention may comprise any type of mutated protein as described above as a ligand, and preferably the ligand present on the solid support may be the polymer.

The solid support of the matrix according to the present invention may be all suitable known ones. Conventional affinity separation matrix is often organic in nature, and it is based on a polymer which exposes its hydrophilic surface such as hydroxyl (—OH), carboxy (—COOH), carboxamido (—CONH$_2$, possibly in N-substituted form), amino (—NH$_2$, possibly in substituted form), oligo- or polyethyleneoxy groups to an aqueous medium which exists in its outside or inside surface if present. The polymer can provide suitable porosity and strength based on, for example, polysaccharides such as dextran, starch, cellulose, pullulan, agarose and the like, advantageously, for example, polysaccharides crosslinked with lower hydrocarbons substituted with bis epoxides, epihalohydrins, 1,2,3-trihalo. Preferably, the solid support is a porous agarose bead. The support used in the present invention may be easily prepared according to standard methods such as inverse suspension gelatinization (S Hjerten: Biochem Biophys Acta 79(2), 393-398 (1964)). Alternatively, the base matrix is a commercially available product, such as Sepharose (trademark) FF (Amersham Biosciences, Uppsala, Sweden). A support which is particularly advantageous for large scale separation is adapted to increase its strength, making the matrix more suitable for high flow rates.

On the other hand, the solid support of the present invention may be based on synthetic polymers such as polyvinyl alcohol, polyhydroxyalkyl acrylate, polyhydroxyalkyl methacrylate, polyacrylamide, polymethacrylamide, and the like. In the case of a hydrophobic polymer such as a matrix based on di-vinyl and mono-vinyl-substituted benzenes, the matrix surface is often hydrophilicized to expose the hydrophilic groups as described above to the surrounding aqueous liquid. These polymers are readily prepared according to standard methods, for example, see the literature ("Styrene based polymer supports developed by suspension polymerization", R. Arshady: Chimica eL'Industria 70(9), 70-75 (1988)). Alternatively, a commercial product such as Source (trademark) (Amersham Biosciences, Uppsala, Sweden) is used.

In addition, the solid support according to the present invention may comprise a support of an inorganic nature such as silica, zirconium oxide, and the like, while the solid support may be in other forms such as a surface, chip, capillary or filter.

Regarding the shape of the matrix according to the invention, the matrix may be in the form of a porous monolith. Alternatively, the matrix may be one of bead or particle type, which may be porous or non-porous. Beads or particle type matrix may be used as a filled beds or in a suspended form. Suspended forms include those known as extended beds and pure suspensions in which particles or beads move freely. In the case of monolith, filled beds and extended beds, a separation process is usually preceded by conventional chromatography with a concentration gradient.

The ligand may be attached to the support via conventional coupling techniques using, for example, an amino group and/or a carboxyl group present in the ligand. Bisepoxide, epichlorohydrin, CNBr, N-hydroxysuccinimide (NHS) and the like are well known coupling agents. Between the support and the ligand, molecules known as spacers may be introduced, which will improve the utilization of the ligand and facilitate the chemical coupling of the ligand to the support. Alternatively, the ligand may be attached to the support by non-covalent bond, such as by physical adsorption or biospecific adsorption.

The present invention provides a method for isolating an immunoglobulin, such as IgG, IgA and/or IgM, in which a mutated protein, a polymer or a matrix according to the invention are used. Preferably, the method may be a method of isolating an immunoglobulin using a matrix.

More specifically, the immunoglobulin isolation method of the present invention comprises the following steps of:

a) providing a solution comprising an immunoglobulin as a sample;

b) adsorbing the sample with the mutated protein, polymer or matrix;

c) washing the matrix for chromatography, thereby removing unbound contaminants; and d) recovering a target molecule from the matrix.

Each step will be herein after described in detail.

The step a) is a step of provide a solution comprising an immunoglobulin as a sample.

As used herein, the term 'immunoglobulin' means a generic term for a protein that plays an important role in immunity among serum components and functions as an antibody. Its basic structure is composed of one pair L-chain (light chain) of about 23,000 in molecular weight and one pair of H-chain (heavy chain) of 50,000 to 70,000 in molecular weight by S—S bridging, while being classified as IgG, IgA, IgM, IgD or IgE according to the type of H-chain.

In the step (b), the sample of step (a) is adsorbed to the above mutated protein, polymer or matrix.

Preferably, after setting an appropriate conditions (for example, pH, salt concentration, etc) under which the immunoglobulin contained in the sample can be adsorbed to the ligand present on the matrix, the flow of the sample is made so sufficiently slow as to pass through the matrix causing the immunoglobulin to be sufficiently adsorbed on to the matrix.

As described above in the present invention, the mutated protein comprises an amino acid sequence as defined in SEQ ID NO: 2 or a functional variant thereof, the polymer means a protein comprising the mutated protein as a protein which comprises unit two or more repeat units, the matrix means a matrix for chromatography where in a plurality of ligands comprising the immunoglobulin-binding protein are coupled to a solid support.

The step c) is a step of washing the matrix for chromatography of step b) to remove unbound contaminants.

Preferably, the matrix is washed with an aqueous solution or an alkaline agent used for the sample to remove unbound substances or contaminants.

The step d) is a step of recovering the target molecule from the matrix of step c).

Preferably, the matrix in which the unbound substances or contaminants are removed is passed through an eluent or a solution having high affinity with the target molecule, thereby isolating the target molecule. More preferably, this step may isolate an immunoglobulin.

Accordingly, the present invention provides a chromatographic method in which one or more target compounds are separated from a liquid by adsorption to said mutated protein or polymer or matrix. The desired product may be a separate compound or liquid. Thus, this aspect of the invention relates to affinity chromatography, a widely used and well-known separation technique. Briefly, in the first step, preferably, a solution comprising an antibody as described above is passed through the separation matrix under conditions which allow the target compound to adsorb to the ligand present on the separation matrix. These conditions are controlled, for example, by the pH and/or the salt concentration, i.e. the ionic strength in the solution. Care should be taken not to exceed the capacity of the matrix, that is, the flow should be slow enough to allow satisfactory adsorption. At this step, the other components of the solution will in principle pass through without clogging. As an unrequired step to remove retained materials and/or loosely bound materials, the matrix is then washed by using an aqueous solution or the like. As described herein, the matrix is most advantageously used through a washing step using an alkaline agent, as described above. Subsequently, the second solution, referred to as an eluent is passed over the matrix under conditions that allow desorption, i.e. release, of the target compound. These conditions are usually provided by changes in pH, salt concentration, i.e., ionic strength, hydrophobicity, and the like. Various elution methods such as gradient elution and stepwise elution are known. Elution may be possible with a second solution comprising a competing substance to replace the desired antibody on the matrix. A general overview of the principles of affinity chromatography is given, for example, in the literature (Wilchek, M., and Chaiken, I. 2000, An overview of affinity chromatography, Methods Mol. Biol. 147:1-6).

The present invention provides a method, i.e., a chromatographic method, in which one or more target compounds are separated, comprising the following steps of:

a) providing a solution comprising a target compound as a sample;

b) passing the sample through the mutated protein, polymer or matrix to adsorb the target compound to a ligand on the matrix;

c) washing the matrix for chromatography to remove loosely bound substances and unbound substances; and d) passing an eluent over the matrix to elute the target compound.

Each step will be described in detail below.

The step a) is a step of providing a solution comprising a target compound as a sample.

As used herein, the term 'target compound' refers to a protein with an increased alkali tolerance which is purified by a mutated immunoglobulin-binding protein, and may preferably be immunoglobulin.

The step b) is a step of passing the sample of step a) through the mutated protein, polymer or matrix to adsorb the target compound to the ligand on the matrix.

As described above, preferably, after setting an appropriate conditions (for example, pH, salt concentration, etc) under which the immunoglobulin contained in the sample can be adsorbed to the ligand present on the matrix, the flow of the sample is made so sufficiently slow as to pass through the matrix causing the immunoglobulin to be sufficiently adsorbed on to the matrix.

The step c) is a step of washing the chromatographic matrix of step b) to remove loosely bound substances and unbound substances.

Preferably, the matrix is washed with an aqueous solution or an alkaline agent used for the sample to remove loosely bound substances, unbound substances or contaminants.

The step d) is a step of passing an eluent over the matrix of step c) to elute the target compound.

Preferably, the matrix in which the unbound substances or contaminants are removed is passed through an eluent or a solution having high affinity with the target molecule, thereby isolating the target molecule. More preferably, this step may isolate an immunoglobulin.

The present invention provides an immunoglobulin protein isolated by the immunoglobulin isolation method.

Also, the present invention provides a target compound isolated by the chromatographic method.

The immunoglobulin-binding protein is the same as described above.

Advantageous Effect

The present invention can provide an immunoglobulin-binding protein ligand and a matrix for antibody purification with an improved alkali tolerance and stability against various alkali washing.

BRIEF DESCRIPTION OF DRAWINGS/FIGURES

MODE FOR CARRYING OUT INVENTION

Figure 1:
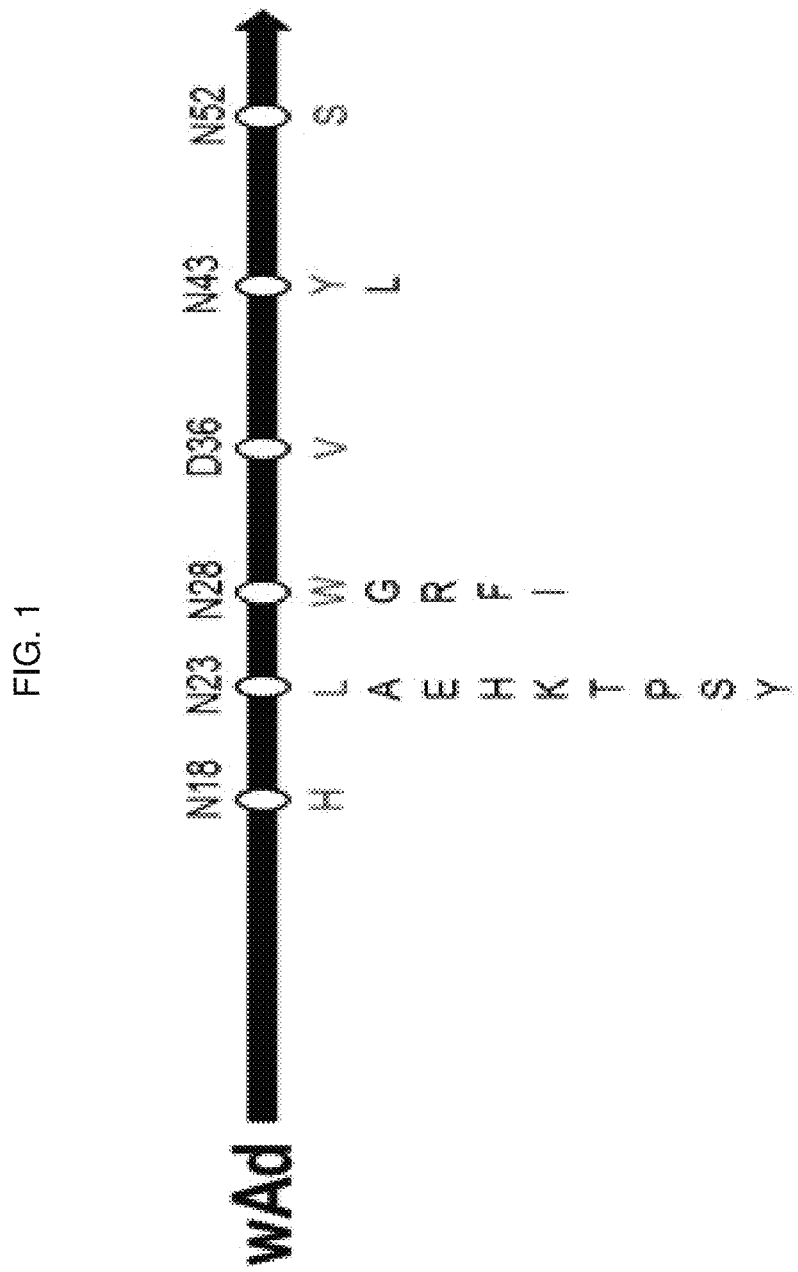
FIG. 1 is information of residues selected by a modified experiment for an increased alkali tolerance.

Hereinafter, the present invention will be described in detail.

However, the following Examples are only illustrative of the present invention, which is not limited by the following examples.

Example 1: Production of Fc Protein of Recombinant Immunoglobulin G for Improvement 1-1. Synthesis of Fc Domain Gene of Immunoglobulin G The sequence encoding the Fc polypeptide from human IgG1 was found through Blast at the NCBI site (GenBank accession no. Y14735) and was synthesized by Cosmogenetech (Daejeon, Republic of Korea).

1-2. Preparation of pET-Fc Plasmid

A pET-Fc plasmid was prepared by inserting the Fc gene obtained in Example 1-1 into the NdeI and XhoI restriction enzyme recognition sites of the pET29a (+) vector (Stratagene, USA). The details are as follows:

The Fc gene DNA product obtained by the synthesis in Example 1-1 was digested with restriction enzymes NdeI and XhoI, and then purified with a purification kit (QIAEX Gel Extraction Kit; Qiagen, Germany), and used as an insert DNA. Also, a DNA fragment in which pET29a (+) vector DNA was digested with restriction enzymes NdeI and XhoI and dephosphorylated with CIP was used as a vector DNA. The inserted DNA and vector DNA were ligated at 16° C. for 12 to 16 hours using T4 DNA ligase (Roche, Germany), and then transformation was performed on *E. coli* BL21 (DE3) for expression by electrophoration using the ligation solution. The strain was plated on LB agar medium containing kanamycin antibiotic at a concentration of 40 μg/mL and transformants were selected by incubating at 37° C. overnight. A plasmid was isolated from the transformant, and the nucleotide sequence of the inserted DNA was determined. Thus, a pET-Fc plasmid containing the Fc gene having the nucleotide sequence of SEQ ID NO: 12 was prepared. The pET-Fc plasmid expresses the wild-type Fc protein defined by SEQ ID NO: 13.

1-3. Protein Purification Using Nickel-Affinity Resin

In order to cultivate *E. coli* BL21 (DE3) transformants, these were inoculated into a 50 mL conical tube in which 5 mL of LB liquid medium containing kanamycin antibiotic was dispensed, followed by shake culture at 37° C. and 200 rpm for 16 hours. The culture was inoculated with 1% (v/v) of the culture medium in a 500 mL Erlenmeyer flask containing 200 mL of LB liquid medium followed by shake culture at 37° C. and 200 rpm. Isopropyl-β-D-thio-galactopyranoside (IPTG) was added to obtain its final concentration of 1 mM at $OD_{600}$=about 0.6, followed by additional shake culture at 37° C. and 200 rpm for 18 hours. After the culture broth of the flask was centrifuged (4° C., 10000 rpm, 30 min) and the cells were recovered, suspended in 10 mL of a PBS buffer (pH 7.4) (iNtRON Biotechnology, Inc. Republic of Korea) solution and disrupted at 4° C. for 15 minutes by an ultrasonic disintegrator, and then centrifuged at 4° C., 10,000 rpm for 30 minutes to collect only a supernatant. The column filled with 1 mL of Nickel-affinity resin, NiNTA Chelating Agarose CL-6B (Incospharm, Republic of Korea) was flowed with 5 mL of binding buffer (20 mM $NaH_2PO_4$, 30 mM NaCl, 10 mM Imidazole pH 7.4), and 2.5 mL of the supernatant and 5 mL of binding buffer are mixed and flowed into the column. After 5 mL of wash buffer (20 mM $NaH_2PO_4$, 30 mM NaCl, 20 mM Imidazole pH 7.4) was flowed, taking 2.5 mL of elution buffer (20 mM $NaH_2PO_4$, 30 mM NaCl, 300 mM Imidazole pH 7.4) into a 15 mL conical tube. Purified protein was desalted using PD10 column.

Example 2: Construction of a Domain Expression Vector of Protein a Derived from *Staphylococcus aureus*

2-1. Synthesis of a Domain Gene

The gene of the A domain, the third domain of Protein A derived from *Staphylococcus aureus*, was synthesized as one containing HQ tag by Cosmogenetech (Daejeon, Republic of Korea), considering the subsequent protein purification.

2-2. Preparation of pBC-wAd Plasmid

A pBC-wAd plasmid was prepared by inserting the A domain gene obtained in Example 1-1 into the NdeI and NotI restriction enzyme recognition sites of pBC KS (+) vector (Stratagene, USA). The details were as follows. The wAd gene DNA product obtained by the synthesis in the above Example 2-1 was digested with restriction enzymes NdeI and NotI, purified with a purification kit (QIAEX Gel Extraction Kit; Qiagen, Germany) and used as an insert DNA. Also, a DNA fragment in which pBC KS (+) vector DNA was digested with restriction enzymes NdeI and NotI and dephosphorylated with CIP was used as a vector DNA. After the inserted DNA and vector DNA were ligated using T4 DNA ligase at 16° C. for 12 to 16 hours, *E. coli* DH5α was transformed by electrophoration using the above-mentioned ligation solution. The strain was plated on LB agar medium containing chloramphenicol antibiotics at a concentration of 20 μg/mL, and the transformants were selected by incubating at 37° C. overnight. A plasmid was isolated from the transformant, and the nucleotide sequence of the inserted DNA was determined. Thus, a pBC-wAd plasmid containing the wild type A domain gene having the nucleotide sequence of SEQ ID NO: 1 was prepared. The pBC-wAd plasmid expresses the wild-type A domain protein defined by SEQ ID NO: 2.

Example 3: wAd Improvement Using Error-Prone PCR Method 3-1. Preparation of wAd Mutant Library by Error Prone PCR To artificially induce a random mutation in the nucleotide sequence of the synthesized wAd gene, a mutant library was prepared by performing error prone PCR. The procedure for preparing a specific mutant library is as follows: Error prone PCR was induced to produce 1-2 mutations per 1000 bp using a Diversity Random Mutagenesis kit (Clontech, USA), PCR reaction solution was comprised of 1 ng of pBC-wAd plasmid as template DNA, 10 pmol of each of EP-F primer (SEQ ID NO: 14) and T7 primer (SEQ ID NO: 15), 40 μM dGTP, Diversity dNTP mix and TITANIUM Taq polymerase, respectively, while its final volume was adjusted to 100 μL. The PCR was performed using Takara PCR Thermal Cycler (Takara, Japan), while its reaction conditions were as follows: the reaction mixture was pre-denatured at 94° C. for 30 seconds, denaturation at 94° C. for 30 seconds, annealing at 55° C. for 30 seconds, and polymerization at 68° C. for 3 minutes which were repeated 16 times and then post-polymerized at 68° C. for 1 minute. The PCR product of each mutant wAd gene obtained by the error prone PCR under the above conditions was digested with restriction enzymes NdeI and NotI, purified using QIAEX Gel Extraction Kit (Qiagen, Germany) and used as an insert DNA, while pBC-KS (+) plasmid was digested with restriction enzymes NdeI and NotI and a recovered DNA fragment of 3.4 kb in size was used as a vector DNA. The inserted DNA and vector DNA were ligated for 16 hours at 16° C. using T4 DNA ligase (New England Biolabs, Sweden), and E. coli DH5α was transformed by electroporation using the ligation solution. The strain was plated on an LB agar medium containing chloramphenicol antibiotics at a concentration of 20 μg/mL and cultured overnight at 37° C. to prepare a random mutant library.

3-2. Selection for Variants with Increased Alkali Tolerance

The E. coli DH5α transformant containing the mutation-induced mutant wAd gene was inoculated in a 96-deep well plate (Bioneer, Republic of Korea) in which 600 μL of the LB liquid medium containing the chloramphenicol antibiotic was dispensed, followed by shake culture in a condition of 37° C. and 280 rpm for 18 hours. The specific protein purification process was carried out using Promega His-Link™ 96 Protein Purification System (Promega, USA). 60 μL of the FastBreak™ Cell Lysis Reagent, 10×/DNase I solution was added to 600 μL of the culture, followed by adding 45 μL of HisLink™ Resin to each well, and mixing at 100 rpm for 30 minutes. The reaction mixture and the resin were transferred to a Filtration plate and filtered using a Vac-Man Vacuum Manifold (Promega, USA) for 10 seconds under vacuum. Next, 250 μL of wash buffer was added to the 96 wells, followed by vacuum for 10 seconds. The same washing process was them repeated three times. 200 μL of elution buffer (100 mM HEPES, 50 mM Imidazole, pH 7.5) was added to the plate, allowed to react for 10 minutes, and then subjected to vacuum for 1 minute to put purified proteins in a new 96-well plate.

The purified wAd mutants were coupled to N-hydroxysuccinimide (NHS)-activated sepharose 4 Fast flow (GE Healthcare, Sweden) in 96-well plates. 150 μl (59.5 μg/mL) of the purified Fc in Example 1-3 was transferred to a filtration plate containing wAd mutants coupled to the NHS-activated sepharose beads, and reacted at room temperature for 1 hour at 100 rpm. Unbound Fc protein was removed by vacuum, and 150 μL of PBS buffer was added, followed by washing under vacuum. This washing procedure was repeated three times. 150 μL of elution buffer (0.1 M Glycine HCl, pH 3.0) was added, reacted at room temperature for 30 seconds, and then subjected to vacuum for 1 minute to put proteins in a new 96-well plate. The filtration plate, which processed the elution buffer, was dispensed with 150 μL of PBS buffer and washed under vacuum. This washing procedure was repeated three times. A new 96-well plate carrying the supernatant was measured for Fc protein content at $OD_{280}$ using a Synergy HTX multi-mode reader (BioTek, USA). To confirm the alkali tolerance of the wAd mutants, 150 μL of 0.5 N NaOH was added to the wAd mutant resin in the filtration plate and reacted at 100 rpm for 6 hours at room temperature, followed by washing three times with PBS buffer, and analyzing the residual Fc binding activity in the same manner as described above.

The absorbance values of the mAEP variants of Example 3-3 before and after treatment with 0.5 N NaOH were compared to select wAd-modified proteins having a greater alkali tolerance than wAd. It was confirmed through a gene sequencing that 6 mutants of AEP1 (N18H) (SEQ ID NO: 3), AEP4 (D36V) (SEQ ID NO: 4), AEP5 (N43Y) (SEQ ID NO: 5), AEP6 (N52S) (SEQ ID NO: 6), AEP2 (N23T) (SEQ ID NO: 7), AEP3 (N28W) (SEQ ID NO: 8) were obtained.

Example 4: WAd Improvement Using Site-Saturation Mutagenesis Method 4-1. Construction of wAd Mutant Library by Site-Saturation Mutagenesis A site-saturation mutagenesis library was constructed for the six amino acid residues (N18, N23, N28, D36, N43, N52) selected in Example 3-2 to further confer alkali tolerance. Specifically, in order to prepare a library in which the 18th amino acid was mutated, AEP1 (SEQ ID NO: 3) inserted into pBC KS (+) vector was used as a template with 18-F primer (SEQ ID NO: 16), 18-R primer (SEQ ID NO: 17), pFU-x Reaction buffer, 10 mM dNTP, pFU-x polymerase obtain to a final volume of 50 μL. Reaction conditions were as follows: the reaction mixture was pre-denatured at 95° C. for 1 minute, while denaturation at 95° C. for 50 seconds, annealing at 53° C. for 50 seconds, and polymerization at 68° C. for 3 minutes, which were repeated 18 times and then post-polymerized at 68° C. for 10 minutes. The PCR product obtained under the above conditions was treated with restriction enzyme DpnI for 18 hours, purified with a purification kit (PCR purification Kit; Cosmogenetech, Republic of Korea), and transformed into E. coli DH5α by electrophoration. The strain was plated on an LB agar medium containing chloramphenicol antibiotics at a concentration of 20 μg/mL and incubated overnight at 37° C. to prepare a site-saturation mutagenesis library.

Thereafter, a library was constructed using 36-F primer (SEQ NO ID: 20) and 36-R primer (SEQ NO ID: 21), 43-F primer (SEQ NO ID: 22) and 43-R primer (SEQ NO ID: 23), 52-F primer (SEQ NO ID: 24) and 52-R primer (SEQ NO ID: 25), 23-F primer (SEQ NO ID: 26) and 23-R primer (SEQ NO ID: 27), 28-F primer (SEQ NO ID: 28) and 28-R primer (SEQ NO ID: 29), respectively, using AEP4 (SEQ NO ID: 4), AEP5 (SEQ NO ID: 5), AEP6 (SEQ NO ID: 6), AEP2 (SEQ NO ID: 7), and AEP3 (SEQ NO ID: 8) as a template inserted in the pBC KS (+) vector in the same manner as described above.

4-2. Selection of Mutants with Increased Alkali Tolerance

Figure 2:
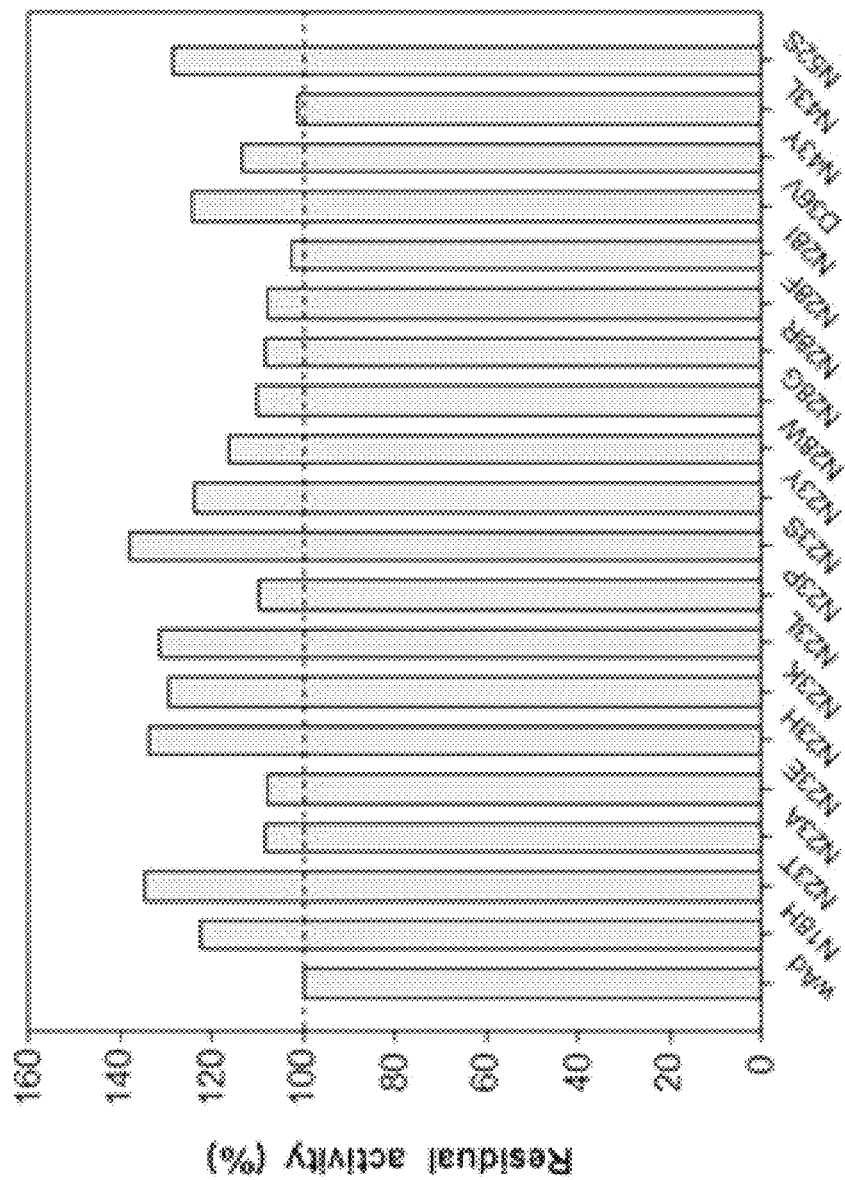
FIG. 2 is a graph showing the increased alkali tolerance of mutated A domains selected by the modified experiment.

As a result of searching the library using the same method as in Example 3-2, AES (N23A), AES (N23E), AES (N23H), AES (N23K), AES (N23L), AES (N23P), AES (N23S), AES (N23Y), AES (N28G), AES (N28R), AES (N28F), AES (N28I), and AES (N43L) were further selected as a mutant with increased alkali tolerance compared to wAd (FIG. 2), respectively.

Example 5: Development of Final mAd Variants with Increased Alkali Tolerance 5-1. mAF Gene Synthesis With reference to the substitution residues selected in Example 4, the residues having the highest residual activity at the site of the mutation were introduced into wAd. A mutant N18H/N23L/N28W/D36V/N43Y/N52S was designed and designated as mAF (SEQ ID NO: 9), while its gene containing HQ tag was synthesized by Cosmogenetech (Daejeon, Republic of Korea).

5-2. Preparation of pBC-mAF Plasmid

The mAF gene obtained in Example 5-1 was cloned into a pBC KS (+) vector in the same manner as in Example 1-2, thereby preparing a pBC-mAF plasmid. The pBC-mAF plasmid expresses the mAF protein of SEQ ID NO: 10.

5-3. Comparison of Alkali Tolerance of Mutant Protein mAF Monomer

Figure 3:
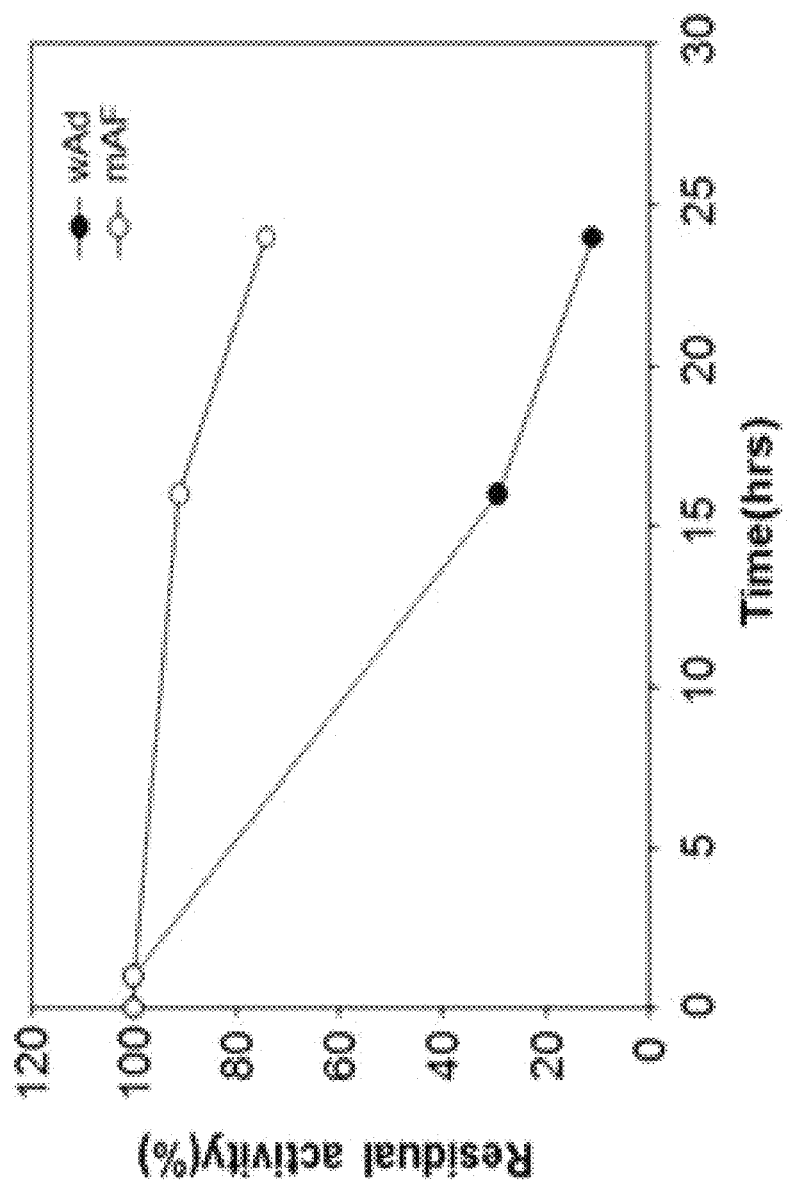
FIG. 3 is a graph comparing the alkali tolerance between the mutated A domain (mAF) reflecting all the residues contributing to alkali tolerance and the wild type A domain (wAd).

The protein purification was carried out in the same manner as in Example 1-4, and the alkali tolerance over time was compared in the same manner as in Example 3 (FIG. 3).

As a result, as shown in FIG. 3, when the activity of the mAF protein according to the present invention was compared with its activity after treatment with 0.5 N NaOH for 24 hours, it was confirmed that the alkaline resistance was increased by about 7 times as compared with the wAd protein having the wild-type amino acid sequence.

Example 6: Evaluation on Alkali Tolerance of mAF Tetramer

6-1. Preparation of pET-4mAF Plasmid

To confirm the alkali tolerance results of Example 5-3, the mAF gene was prepared as a tetramer by performing PCR. The details were as follows.

In order to prepare the mAF gene tetramer, a PCR was performed in which mAF was used as a template and mAf2-F primer (SEQ NO ID: 28) and mAF2-R primer (SEQ NO ID: 29) were used to randomly ligate genes. The PCR reaction mixture was comprised of each template DNA, primer, pfu-x buffer, dNTPs mix, and pfu-x polymerase, while its final volume was adjusted to 100 µl. The PCR reaction conditions were as follows: the reaction mixture was pre-denatured at 96° C. for 2 minute, while denaturation at 96° C. for 30 seconds, annealing at 54° C. for 30 seconds, and polymerization at 72° C. for 1 minutes, were repeated 25 times and then post-polymerized at 72° C. for 5 minutes. The obtained PCR products were purified using a purification kit, QIAEX Gel Extraction Kit (Qiagen, Germany). The mAF gene was ligated at 16° C. for 12 to 16 hours using T4 DNA ligase (Roche, Germany), and then a 0.72 kb tetrameric mAF gene product was recovered using a purification kit (QIAEX Gel Extraction Kit; Qiagen, Germany). The PCR was performed in the same manner as described above, while using the recovered tetrameric mAF gene as a template, 4mAF-F primer (SEQ ID NO: 30) and 4mAF-R primer (SEQ ID NO: 31). The resulting PCR product was recovered a 0.72 kb tetramer mAF gene DNA product using a purification kit (QIAEX Gel Extraction Kit; Qiagen, Germany), after digestion with the restriction enzymes NdeI and XhoI, 0.72 kb of the tetramer mAF gene DNA was purified with a purification kit (QIAEX Gel Extraction Kit; Qiagen, Germany) which was then it used as an insert DNA. Further, a DNA fragment obtained by digesting pET29a (+) vector DNA with restriction enzymes NdeI and XhoI, and dephosphorylating with CIP was used as a vector DNA. The inserted DNA and vector DNA were ligated at 16° C. for 12 to 16 hours using T4 DNA ligase (Roche, Germany), and then transformation was performed on *E. coli* BL21 (DE3) for expression by electrophoration using the ligation solution. The strain was plated on LB agar medium containing kanamycin antibiotic at a concentration of 40 µg/mL and transformants were selected by incubating at 37° C. overnight. A plasmid was isolated from the transformant, and the nucleotide sequence of the inserted DNA was determined thereby preparing, a pET-Fc plasmid containing the 4mAF gene having the nucleotide sequence of SEQ ID NO: 11. The pET-4mAF plasmid expresses the mutant 4mAF protein defined by SEQ ID NO: 32.

6-2. Purification of Mutant Protein mAF Tetramer Using Nickel-Affinity Resin In order to culture *E. coli* BL21 transformants, 5 mL of a TB liquid medium containing kanamycin antibiotic was inoculated into a 50 mL test tube, followed by shake culture in a condition of 37° C. and 200 rpm for 16 hours.

The culture solution was inoculated with 1% (v/v) of the starter culture into a 2000 mL Erlenmeyer flask in which 500 mL of TB liquid medium was dispensed, and then shaking cultured at 37° C. and 200 rpm, isopropyl-β-D-thio-galactopyranoside (IPTG) was added to obtain its final concentration of 1 mM at about $OD_{600}$=0.6, followed by additional shaking at 37° C. and 200 rpm for 18 hours. After the culture broth of the flask was centrifuged (4° C., 10000 rpm, 30 min) and the cells were recovered, suspended in 20 mL of a PBS buffer solution (pH 7.4) (iNtRON Biotechnology, Inc., Republic of Korea) and disrupted at 4° C. for 35 minutes by an ultrasonic disintegrator, and then centrifuged at 10,000 rpm for 30 minutes at 4° C. to obtain only supernatant. The column filled with 5 mL of Ni NTA Chelating Agarose CL-6B (Incospharm, Republic of Korea) was flowed with 25 mL of binding buffer (20 mM $NaH_2PO_4$, 30 mM NaCl, 10 mM Imidazole pH 7.4), while 20 mL of the supernatant and 40 mL of binding buffer are mixed and flown into the column. After 25 mL of wash buffer (20 mM $NaH_2PO_4$, 30 mM NaCl, 20 mM Imidazole pH 7.4) is flown, 40 mL of elution buffer (20 mM $NaH_2PO_4$, 30 mM NaCl, 300 mM Imidazole pH 7.4) was placed into a 50 mL conical tube. Purified protein was desalted using PD10 column.

6-3. Comparison of Alkali Tolerance of Mutant Protein mAF Tetramer

4mAF purified in Example 6-2 was coupled to N-hydroxysuccinimide (NHS)-activated sepharose 4 Fast flow (GE Healthcare, Sweden). The prepared 4mAF resin was compared with a commercialized resin MabSelect Sure (GE Healthcare Life Sciences, USA) which is known to be highly resistant to alkali, for alkali tolerance. 100 µl of resin and 5 mL of 0.5 N NaOH were added to the disposable columns, sealed, and then gently shaken for alkaline treatment. After a certain period of time, the seal was removed, and NaOH was removed by gravity-dripping, and the resin was washed 5 times with PBS buffer (pH 7.4) (iNtRON Biotechnology, Inc., Republic of Korea). 5 mL of 2 mg/mL rabbit-derived purified antibody (Youngin frontier, Republic of Korea) was mixed with the resin, sealed again, and allowed to react at room temperature for 3 hours with gentle shaking. Unbound antibody protein was removed by gravity-dripping and washed three times with PBS buffer. 3 mL of elution buffer (0.1 M GlycineHCl, pH 3.0) was flown to separate the bound antibody. The separated antibody was collected in a tube containing 300 µl of the neutralization buffer (1M Tris-HCl, pH 8.5) and the amount of recovered protein was measured. After the binding assay was completed, the elution buffer and PBS buffer were washed alternately and further mixed with 5 mL of 0.5 N NaOH for further alkali treatment.

Figure 4:
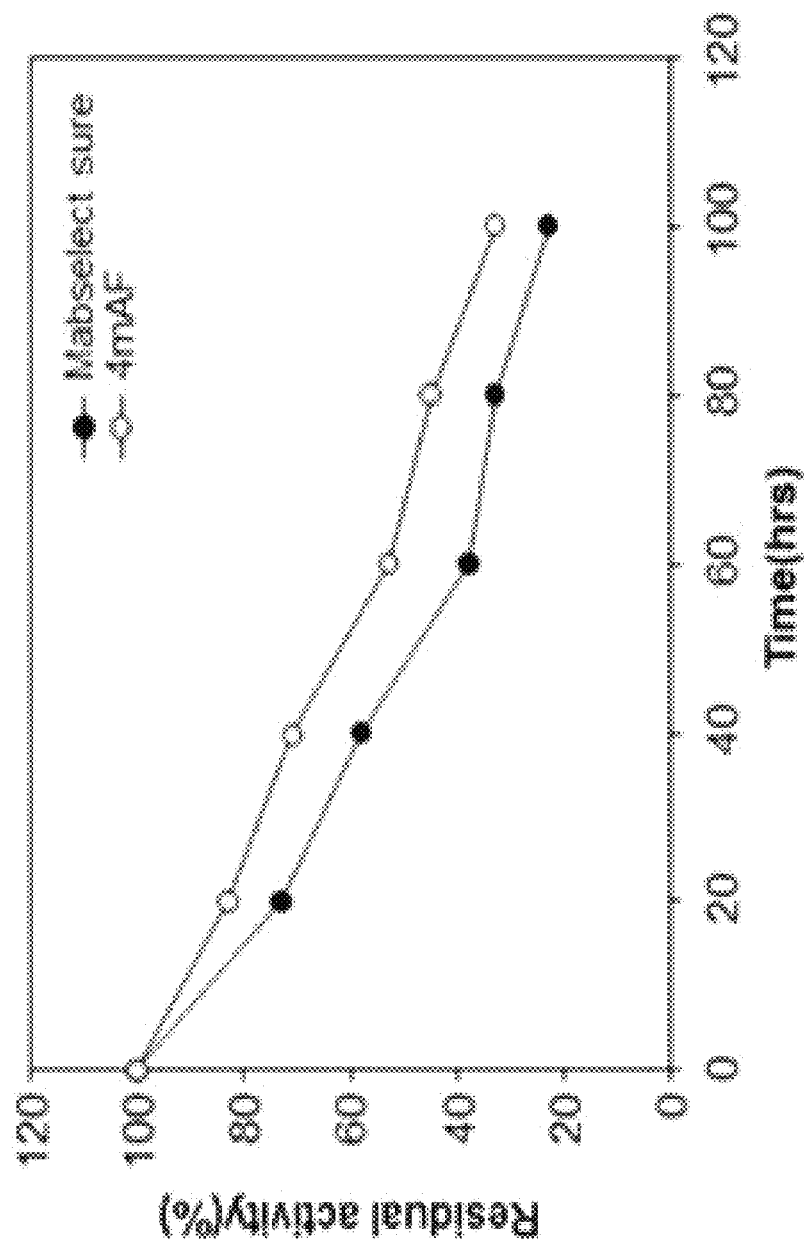
FIG. 4 is a graph showing a comparison between a commercialized resin (Mabselecture) and a resin prepared as a mutated A domain tetramer (4mAF) reflecting all the residues contributing to alkali tolerance.

As a result, as shown in FIG. 4, the 4mAF resin of the present invention was found to be superior in alkali tolerance to MabSelect Sure, which is widely used in industry. Residual activity of 4 mAF was 33% in alkaline treatment for 100 hours, which was 1.4 times higher than that of MabSelect Sure.

INDUSTRIAL APPLICABILITY

The present invention provides the immunoglobulin-binding protein ligand and the matrix for antibody purification with improved alkali tolerance and stability against multiple alkali washings, which has an excellent industrial applicability.

What is claimed is:

1. An immunoglobulin-binding protein defined by SEQ ID NO: 2 of which an amino acid residue at one or more positions selected from the group consisting of 18th, 36th, 43th and 52nd positions is mutated, wherein the mutation is at one or more positions selected from the group consisting of N18H, D36V, N43Y/L and N52S.

2. The immunoglobulin-binding protein of claim 1, further comprising the mutation of an amino acid residue at one or more positions selected from the group consisting of 23rd and 28th positions in the protein.

3. The immunoglobulin-binding protein of claim 2, wherein the mutation at the 23rd position is a mutation selected from the group consisting of N23T, N23A, N23E, N23H, N23K, N23L, N23P, N23S and N23Y, and wherein the mutation at the 28th position is a mutation selected from the group consisting of N28W, N28G, N28R, N28F and N28I.

4. The immunoglobulin-binding protein of claim 2, wherein the immunoglobulin-binding protein has an amino acid sequence as defined by SEQ ID NO: 9.

5. A polymer comprising the mutated protein of claim 1 as a protein unit, wherein the polymer comprises two or more repeat units.

6. The polymer of claim 5, further comprising at one or more of E, D, A, B and C domains of *Staphylococcus* protein A.

7. A matrix for chromatography wherein a plurality of ligands comprising the immunoglobulin-binding protein of claim 1 are coupled to a solid support.

* * * * *